United States Patent

Krenzer et al.

[11] 4,097,485
[45] Jun. 27, 1978

[54] THIAZOLYLIMIDAZOLIDINONE ESTERS OF FURYL AND THIENYL SUBSTITUTED ACIDS

[75] Inventors: John Krenzer, Oak Park; Chin Ching Wu, Libertyville, both of Ill.

[73] Assignee: Velsicol Chemical Corporation, Chicago, Ill.

[21] Appl. No.: 697,294

[22] Filed: Jun. 17, 1976

[51] Int. Cl.$^2$ .......................................... C07D 285/12
[52] U.S. Cl. ................................. 260/306.8 D; 71/90
[58] Field of Search ...................... 260/306.8 R; 71/90

[56] References Cited

U.S. PATENT DOCUMENTS

| | | | |
|---|---|---|---|
| 4,043,795 | 8/1977 | Krenzer | 71/90 |
| 4,046,768 | 9/1977 | Krenzer et al. | 71/90 |
| 4,052,193 | 10/1977 | Krenzer | 71/90 |
| 4,053,298 | 10/1977 | Krenzer | 71/90 |
| 4,056,383 | 11/1977 | Krenzer | 71/90 |

*Primary Examiner*—Donald G. Daus
*Assistant Examiner*—D. B. Springer

*Attorney, Agent, or Firm*—Robert J. Schwarz; Dietmar H. Olesch

[57] ABSTRACT

This invention discloses new compounds of the formula

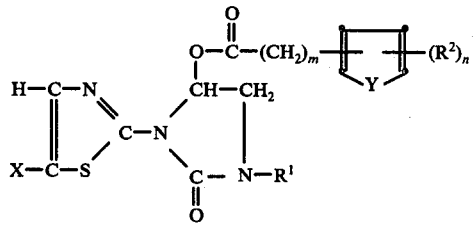

wherein X is selected from the group consisting of halogen and alkylsulfonyl; $R^1$ is selected from the group consisting of alkyl, alkenyl, haloalkyl and alkynyl; m is an integer from 0 to 3; Y is selected from the group consisting of oxygen and sulfur; $R^2$ is selected from the group consisting of alkyl and halogen; and n is an integer from 0 to 2.

9 Claims, No Drawings

THIAZOLYLIMIDAZOLIDINONE ESTERS OF FURYL AND THIENYL SUBSTITUTED ACIDS

This invention relates to new compositions of matter and more specifically relates to new chemical compounds of the formula

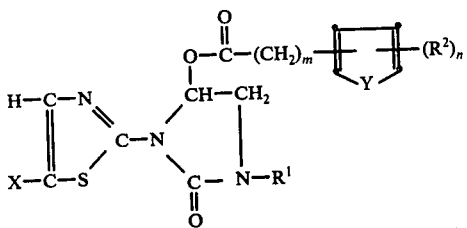
(I)

wherein X is selected from the group consisting of halogen and alkylsulfonyl; $R^1$ is selected from the group consisting of alkyl, alkenyl, haloalkyl and alkynyl; m is an integer from 0 to 3; Y is selected from the group consisting of oxygen and sulfur; $R^2$ is selected from the group consisting of alkyl and halogen; and n is an integer from 0 to 2.

The compounds of the present invention are useful as herbicides.

In a preferred embodiment of the present invention X is selected from the group consisting of chlorine, bromine, fluorine and lower alkylsulfonyl; $R^1$ is selected from the group consisting of lower alkyl, lower alkenyl, lower haloalkyl and propargyl; m is an integer from 0 to 3; Y is selected from the group consisting of oxygen and sulfur; $R^2$ is selected from the group consisting of lower alkyl, chlorine, bromine and fluorine, and n is an integer from 0 to 2.

The term "lower" as used herein designates a straight or branched carbon chain of up to six carbon atoms.

The compounds of this invention can be prepared by reacting a compound of the formula

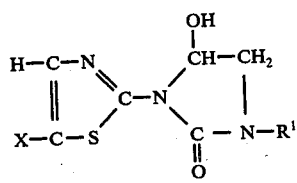
(II)

wherein X and $R^1$ are as heretofore described, with an acid chloride of the formula

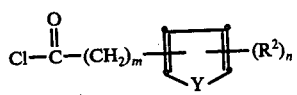
(III)

wherein m, Y, $R^2$ and n are as heretofore described, in the presence of an acid acceptor such as a tertiary amine. This reaction can be effected by slowly adding the acid chloride of formula III with stirring to a solution of an about equimolar amount of the compound of formula II in an inert organic solvent, in the presence of the acid acceptor, at a temperature of about 0° to 30° C. After the addition is completed, the reaction mixture can be heated at a temperature ranging up to the reflux temperature of the mixture to ensure completion of the reaction. The desired product can then be recovered by first filtering the reaction mixture to remove acid acceptor chloride, followed by stripping off the solvent if the product is soluble therein, or, if formed as a precipitate, by filtration and subsequent washing and purification.

The compounds of formula II can be prepared by heating a compound of the formula

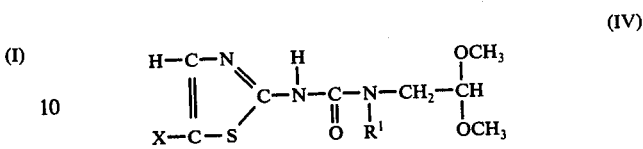
(IV)

wherein X and $R^1$ are as heretofore described, in a dilute, aqueous, acidic reaction medium for a period of from about 10 to about 60 minutes. Temperatures of from about 60° C to the reflux temperature of the reaction mixture can be utilized. The reaction medium can comprise a dilute, aqueous, inorganic acid such as hydrochloric acid at a concentration of from about 0.5 to about 10 percent. Lower water-miscible alkanols can also be suitably added to the reaction medium to aid in the dissolution of the starting materials. After completion of the reaction the desired product can be recovered upon evaporation of the solvents used if soluble therein or by filtration if formed as a precipitate. This product can then be used as such or can be further purified by standard techniques such as trituration, recrystallization, washing and the like.

The compounds of formula IV can be prepared by reacting a molar amount of an isocyanate dimer of the formula

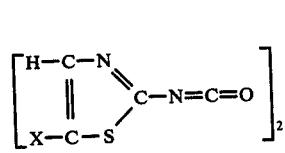
(V)

wherein X is as heretofore described, with about two molar amounts of a dimethyl acetal of the formula

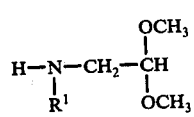
(VI)

wherein $R^1$ is as heretofore described. This reaction can be effected by combining the isocyanate dimer of formula V dissolved in an inert organic solvent such as benzene with the acetal of formula VI at room temperature and stirring the resulting mixture for a period of about ½ to about 4 hours. After this time the reaction mixture can be filtered and the filtrate stripped of solvent to yield the desired product. This product can be used as such or further purified if desired by standard techniques.

The isocyanate dimer of formula V can be prepared by reacting a thiazole of the formula

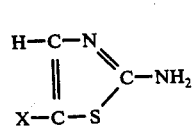
(VII)

wherein X is as heretofore described, with phosgene. This reaction can be effected by adding a slurry or solution of the thiazole in a suitable organic solvent such as ethyl acetate to a solution of phosgene in a similar solvent. The resulting mixture can then be heated at reflux for a period of from ½ to 2 hours. The desired product can then be recovered by filtration if formed as a precipitate or upon evaporation of the organic solvent if soluble therein.

Exemplary suitable compounds of formula VI for preparing the compounds of the present invention are the dimethyl acetal of 2-methylaminoacetaldehyde, the dimethyl acetal of 2-ethylaminoacetaldehyde, the dimethyl acetal of 2-propylaminoacetaldehyde, the dimethyl acetal of 2-allylaminoacetaldehyde, the dimethyl acetal of 2-β-bromoethylaminoacetaldehyde, the dimethyl acetal of 2-propargylaminoacetaldehyde and the like.

Exemplary suitable compounds of formula VII for preparing the compounds of this invention are 2-aminothiazole, 2-amino-5-methylsulfonylthiazole, 2-amino-5-chlorothiazole, 2-amino-5-ethylsulfonylthiazole, 2-amino-5-bromothiazole, 2-amino-5-fluorothiazole and the like.

Exemplary suitable compounds of formula III for preparing the compounds of the present invention are the acid chlorides of the following acids: 2-furoic acid, 3-furoic acid, 2-thiophenecarboxylic acid, 3-thiophenecarboxylic acid, furyl-2-acetic acid, thiophene-2-acetic acid, 3-(2-furyl)-propionic acid, 3-(2-thiophene)-propionic acid, 4-(2-furyl)-butyric acid, 4-(2-thiophene)-butyric acid, 3-methyl-2-furoic acid, 3,4-dimethyl-2-furoic acid, 4-chloro-3-furoic acid, 5-bromo-2-furoic acid, 4-ethyl-2-furoic acid, 4-propyl-2-furoic acid, 3-methyl-2-thiophenecarboxylic acid, 3,4-dimethyl-2-thiophenecarboxylic acid, 4-chloro-2-thiophenecarboxylic acid, 4-bromo-2-thiophenecarboxylic acid, 4-fluoro-2-thiophenecarboxylic acid, 4-ethyl-3-thiophenecarboxylic acid, 4-propyl-2-thiophenecarboxylic acid, 5-methyl-2-thiophenecarboxylic acid and the like.

The manner in which the compounds of the present invention can be prepared is more specifically illustrated in the following examples.

EXAMPLE 1

Preparation of 5-Bromothiazol-2-yl Isocyanate Dimer

2-Amino-5-bromothiazole (19.0 grams) and a saturated solution of phosgene in ethyl acetate (200 ml) were charged into a glass reaction vessel equipped with a mechanical stirrer, thermometer and reflux condenser. The reaction mixture was heated at reflux with stirring for a period of about 3 hours. After this time the reaction mixture was cooled and filtered to recover the desired product 5-bromothiazol-2-yl isocyanate dimer as a fine yellow powder.

EXAMPLE 2

Preparation of the Dimethyl Acetal of 2-[1-Methyl-3-(5-bromothiazol-2-yl)ureido]acetaldehyde 5-Bromothiazol-2-yl isocyanate dimer (17.0 grams), benzene (70 ml) and the dimethyl acetal of 2-methylaminoacetaldehyde (13.5 grams) were charged into a glass reaction vessel equipped with a mechanical stirrer and thermometer. The reaction mixture was then stirred at room temperature for a period of about one hour. After this time the reaction mixture was filtered, and the filtrate was stripped of solvent under reduced pressure, leaving an oil. This oil was chromatographed on silica gel using ethyl acetate as the diluant. The eluant was dissolved in an ethanol-water mixture, and the solution was filtered. The filtrate was then stripped of solvents under vacuum to yield the desired product the dimethyl acetal of 2-[1-methyl-3-(5-bromothiazol-2-yl)ureido]acetaldehyde as a crystalline solid having a melt point of 72° to 73° C.

EXAMPLE 3

Preparation of 1-(5-Bromothiazol-2-yl)-3-methyl-5-hydroxy-1,3-imidazolidin-2-one The dimethyl acetal of 2-[1-methyl-3-(5-bromothiazol-2-yl)ureido]acetaldehyde (10 grams), ethanol (80 ml), water (80 ml) and concentrated hydrochloric acid (8 ml) were charged into a glass reaction vessel equipped with a mechanical stirrer, thermometer and reflux condenser. The reaction vessel was purged with nitrogen gas, and the reaction mixture was heated at reflux with stirring for a period of about 15 minutes. After this time the reaction mixture was stripped of solvents under reduced pressure, and the residue was dissolved in ethyl acetate. The resulting solution was washed with saturated aqueous sodium bicarbonate and dried over anhydrous sodium sulfate. The dried solution was then filtered, and the filtrate was stripped of solvent, leaving an oil. This oil solidified upon standing to yield the desired product 1-(5-bromothiazol-2-yl)-3-methyl-5-hydroxy-1,3-imidazolidin-2-one.

EXAMPLE 4

Preparation of 1-(5-Bromothiazol-2-yl)-3-methyl-5-(2-furoyloxy)-1,3-imidazolidin-2-one 1-(5-Bromothiazol-2-yl)-3-methyl-5-hydroxy-1,3-imidazolidin-2-one (0.2 mole), triethylamine (0.25 mole) and benzene (300 ml) are charged into a glass reaction vessel equipped with a mechanical stirrer, thermometer and reflux condenser. 2-Furoyl chloride (0.21 mole) is added dropwise with stirring. After the addition is completed, the reaction mixture is heated with continued stirring for a period of about 45 minutes. After this time the reaction mixture is filtered, and the filtrate is stripped of solvent under reduced pressure to yield a solid residue. This residue is recrystallized to yield the desired product 1-(5-bromothiazol-2-yl)-3-methyl-5-(2-furoyloxy)-1,3-imidazolidin-2-one.

EXAMPLE 5

Preparation of 5-Chlorothiazol-2-yl Isocyanate Dimer

2-Amino-5-chlorothiazole (19.0 grams) and a saturated solution of phosgene in ethyl acetate (200 ml) are charged into a glass reaction vessel equipped with a mechanical stirrer, thermometer and reflux condenser. The reaction mixture is heated at reflux with stirring for a period of about 3 hours. After this time the reaction mixture is cooled and filtered to recover the desired product 5-chlorothiazol-2-yl isocyanate dimer.

EXAMPLE 6

Preparation of the Dimethyl Acetal of 2-[1-Ethyl-3-(5-chlorothiazol-2-yl)ureido]acetaldehyde 5-Chlorothiazol-2-yl isocyanate dimer (17.0 grams), benzene (70 ml) and the dimethyl acetal of 2- ethylaminoacetaldehyde (13.5 grams) are charged into a glass reaction vessel equipped with a mechanical stirrer and thermometer. The reaction mixture is then stirred at room temperature for a period of about one hour. After this time the reaction mixture is filtered, and the filtrate is stripped of solvent under reduced pressure, leaving an oil. This oil is dissolved in an ethanol-water mixture, and the solution is filtered. The filtrate is then stripped of solvents under vacuum to yield the desired product the dimethyl acetal of 2-[1-ethyl-3-(5-chlorothiazol-2-yl)ureido]acetaldehyde.

EXAMPLE 7

Preparation of 1-(5-Chlorothiazol-2-yl)-3-ethyl-5-hydroxy-1,3-imidazolidin-2-one The dimethyl acetal of 2-[1-ethyl-3-(5-chlorothiazol-2-yl)ureido]acetaldehyde (10 grams), ethanol (80 ml), water (80 ml) and concentrated hydrochloric acid (8 ml) are charged into a glass reaction vessel equipped with a mechanical stirrer, thermometer and reflux condenser. The reaction vessel is purged with nitrogen gas, and the reaction mixture is heated at reflux with stirring for a period of about 15 minutes. After this time the reaction mixture is stripped of solvents under reduced pressure, and the residue is dissolved in ethyl acetate. The resulting solution is washed with saturated aqueous sodium bicarbonate and dried over anhydrous sodium sulfate. The dried solution is then filtered, and the filtrate is stripped of solvent to leave the desired product 1-(5-chlorothiazol-2-yl)-3-ethyl-5-hydroxy-1,3-imidazolidin-2-one.

EXAMPLE 8

Preparation of 1-(5-Chlorothiazol-2-yl)-3-ethyl-5-(2-thienylcarbonyloxy)-1,3-imidazolidin-2-one 1-(5Chlorothiazol-2-yl)-3-ethyl-5-hydroxy-1,3-imidazolidin-2-one (0.2 mole), triethylamine (0.25 mole) and benzene (300 ml) are charged into a glass reaction vessel equipped with a mechanical stirrer, thermometer and reflux condenser. 2-Thiophenecarboxylic acid chloride (0.21 mole) is added dropwise with stirring. After the addition is completed, the reaction mixture is heated with continued stirring for a period of about 45 minutes. After this time the reaction mixture is filtered, and the filtrate is stripped of solvent under reduced pressure to yield a solid residue. This residue is recrystallized to yield the desired product 1-(5-chlorothiazol-2-yl)-3-ethyl-5-(2-thienylcarbonyloxy)-1,3-imidazolidin-2-one.

EXAMPLE 9

Preparation of 5-Fluorothiazol-2-yl Isocyanate Dimer

2-Amino-5-fluorothiazole (19.0 grams) and a saturated solution of phosgene in ethyl acetate (200 ml) are charged into a glass reaction vessel equipped with a mechanical stirrer, thermometer and reflux condenser. The reaction mixture is heated at reflux with stirring for a period of about 3 hours. After this time the reaction mixture is cooled and filtered to recover the desired product 5-fluorothiazol-2-yl isocyanate dimer.

EXAMPLE 10

Preparation of the Dimethyl Acetal of 2-[1-Allyl-3-(5-fluorothiazol-2-yl)ureido]acetaldehyde 5-Fluorothiazol-2-yl isocyanate dimer (17.0 grams), benzene (70 ml) and the dimethyl acetal of 2-allylaminoacetaldehyde (13.5 grams) are charged into a glass reaction vessel equipped with a mechanical stirrer and thermometer. The reaction mixture is then stirred at room temperature for a period of about one hour. After this time the reaction mixture is filtered, and the filtrate is stripped of solvent under reduced pressure, leaving an oil. This oil is dissolved in an ethanol-water mixture, and the solution is filtered. The filtrate is then stripped of solvents under vacuum to yield the desired product the dimethyl acetal of 2-[1-allyl-3-(5-fluorothiazol-2-yl)ureido]acetaldehyde.

EXAMPLE 11

Preparation of 1-(5-Fluorothiazol-2-yl)-3-allyl-5-hydroxy-1,3-imidazolidin-2-one The dimethyl acetal of 2-[1-allyl-3-(5-fluorothiazol-2-yl)ureido]acetaldehyde (10 grams), ethanol (80 ml), water (80 ml) and concentrated hydrochloric acid (8 ml) are charged into a glass reaction vessel equipped with a mechanical stirrer, thermometer and reflux condenser. The reaction vessel is purged with nitrogen gas, and the reaction mixture is heated at reflux with stirring for a period of about 15 minutes. After this time the reaction mixture is stripped of solvents under reduced pressure, and the residue is dissolved in ethyl acetate. The resulting solution is washed with saturated aqueous sodium bicarbonate and dried over anhydrous sodium sulfate. The dried solution is then filtered, and the filtrate is stripped of solvent to leave the desired product 1-(5-fluorothiazol-2-yl)-3-allyl-5-hydroxy-1,3-imidazolidin-2-one.

EXAMPLE 12

Preparation of 1-(5-Fluorothiazol-2-yl)-3-allyl-5-(fur-2-ylacetyloxy)-1,3-imidazolidin-2-one 1-(5-Fluorothiazol-2-yl)-3-allyl-5-hydroxy-1,3-imidazolidin-2-one (0.2 mole), triethylamine (0.25 mole) and benzene (300 ml) are charged into a glass reaction vessel equipped with a mechanical stirrer, thermometer and reflux condenser. 2-Furylacetyl chloride (0.21 mole) is added dropwise with stirring. After the addition is completed, the reaction mixture is heated with continued stirring for a period of about 45 minutes. After this time the reaction mixture is filtered, and the filtrate is stripped of solvent under reduced pressure to yield a solid residue. This residue is recrystallized to yield the desired product 1-(5-fluorothiazol-2-yl)-3-allyl-5-(fur-2-ylacetyloxy)-1,3-imidazolidin-2-one.

EXAMPLE 13

Preparation of 5-Iodothiazol-2-yl Isocyanate Dimer

2-Amino-5-iodothiazole (19.0 grams) and a saturated solution of phosgene in ethyl acetate (200 ml) are charged into a glass reaction vessel equipped with a mechanical stirrer, thermometer and reflux condenser. The reaction mixture is heated at reflux with stirring for a period of about 3 hours. After this time the reaction mixture is cooled and filtered to recover the desired product 5-iodothiazol-2-yl isocyanate dimer.

EXAMPLE 14

Preparation of the Dimethyl Acetal of 2-[1-Propargyl-3-(5-iodothiazol-2-yl)ureido]acetaldehyde 5-Iodothiazol-2-yl isocyanate dimer (17.0 grams), benzene (70 ml) and the dimethyl acetal of 2-propargylaminoacetaldehyde (13.5 grams) are charged into a glass reaction vessel equipped with a mechanical stirrer and thermometer. The reaction mixture is then stirred at room temperature for a period of about 1 hour. After this time the reaction mixture is filtered, and the filtrate is stripped of solvent under reduced pressure, leaving an oil. This oil is dissolved in an ethanol-water mixture, and the solution is filtered. The filtrate is then stripped of solvents under vacuum to yield the desired product the dimethyl acetal of 2-[1-propargyl-3-(5-iodothiazol-2-yl)ureido]acetaldehyde.

EXAMPLE 15

Preparation of 1-(5-Iodothiazol-2-yl)-3-propargyl-5-hydroxy-1,3-imidazolidin-2-one The dimethyl acetal of 2-[1-propargyl-3-(5-iodothiazol-2-yl)ureido]acetaldehyde (10 grams), ethanol (80 ml), water (80 ml) and concentrated hydrochloric acid (8 ml) are charged into a glass reaction vessel equipped with a mechanical stirrer, thermometer and reflux condenser. The reaction vessel is purged with nitrogen gas, and the reaction mixture is heated at reflux with stirring for a period of about 15 minutes. After this time the reaction mixture is stripped of solvents under reduced pressure, and the residue is dissolved in ethyl acetate. The resulting solution is washed with saturated aqueous sodium bicarbonate and dried over anhydrous sodium sulfate. The dried solution is then filtered, and the filtrate is stripped of solvent to leave the desired product 1-(5-iodothiazol-2-yl)-3-propargyl-5-hydroxy-1,3-imidazolidin-2-one.

EXAMPLE 16

Preparation of 1-(5-Iodothiazol-2-yl)-3-propargyl-5-(4-fur-2-ylbutanoyloxy)-1,3-imidazolidin-2-one 1-(5-Iodothiazol-2-yl)-3-propargyl-5-hydroxy-1,3-imidazolidin-2-one (0.2 mole), triethylamine (0.25 mole) and benzene (300 ml) are charged into a glass reaction vessel equipped with a mechanical stirrer, thermometer and reflux condenser. 4-(2-Furyl)butyric acid chloride (0.21 mole) is added dropwise with stirring. After the addition is completed, the reaction mixture is heated with continued stirring for a period of about 45 minutes. After this time the reaction mixture is filtered, and the filtrate is stripped of solvent under reduced pressure to yield a solid residue. This residue is recrystallized to yield the desired product 1-(5-iodothiazol-2-yl)-3-propargyl-5-(4-fur-2-ylbutanoyloxy)-1,3-imidazolidin-2-one.

EXAMPLE 17

Preparation of 5-Methylsulfonylthiazol-2-yl Isocyanate Dimer

A saturated solution of phosgene in ethyl acetate (200 ml) is charged into a glass reaction vessel equipped with a mechanical stirrer, thermometer and reflux condenser. 2-Amino-5-methylsulfonylthiazole (0.1 mole) is added with stirring. After the addition is completed, the reaction mixture is heated at reflux for a period of about one hour. After this time the mixture is cooled, and the solid product formed is recovered by filtration. The solid is then dried to yield the desired product 5-methylsulfonylthiazol-2-yl isocyanate dimer.

EXAMPLE 18

Preparation of the Dimethyl Acetal of 2-[1-β-Bromoethyl-3-(5-methylsulfonylthiazol-2-yl)ureido]acetaldehyde 5-Methylsulfonylthiazol-2-yl isocyanate dimer (0.1 mole), the dimethyl acetal of 2-β-bromoethylaminoacetaldehyde (0.2 mole) and benzene (100 ml) are charged into a glass reaction vessel equipped with a mechanical stirrer and thermometer. The reaction mixture is stirred at ambient temperatures for a period of about 1 hour. After this time the reaction mixture is filtered, and the filtrate is stripped of solvent to yield the desired product the dimethyl acetal of 2-[1-β-bromoethyl-3-(5-methylsulfonylthiazol-2-yl)ureido]acetaldehyde as the residue.

EXAMPLE 19

Preparation of 1-(5-Methylsulfonylthiazol-2-yl)-3-β-bromoethyl-5-hydroxy-1,3-imidazolidin-2-one The dimethyl acetal of 2-[1-β-bromoethyl-3-(5-methylsulfonylthiazol-2-yl)ureido]acetaldehyde (15 grams), water (200 ml), methanol (200 ml) and concentrated hydrochloric acid (10 ml) are charged into a glass reaction vessel equipped with a mechanical stirrer, thermometer and reflux condenser. The reaction mixture is heated at reflux for a period of about 15 minutes. After this time the reaction mixture is stripped of solvents under reduced pressure, leaving a residue. This residue is recrystallized to yield the desired product 1-(5-methylsulfonylthiazol-2-yl)-3-β-bromoethyl-5-hydroxy-1,3-imidazolidin-2-one.

EXAMPLE 20

Preparation of 1-(5-Methylsulfonylthiazol-2-yl)-3-β-bromoethyl-5-(3-furoyloxy)-1,3-imidazolidin-2-one 1-(5-Methylsulfonylthiazol-2-yl)-3-β-bromoethyl-5-hydroxy-1,3-imidazolidin-2-one (0.2 mole), triethylamine (0.25 mole) and benzene (300 ml) are charged into a glass reaction vessel equipped with a mechanical stirrer, thermometer and reflux condenser. 3-Furoyl chloride (0.21 mole) is added dropwise with stirring. After the addition is completed, the reaction mixture is heated with continued stirring for a period of about 45 minutes. After this time the reaction mixture is filtered, and the filtrate is stripped of solvent under reduced pressure to yield a solid residue. This residue is recrystallized to yield the desired product 1-(5-methylsulfonylthiazol-2-yl)-3-β-bromoethyl-5-(3-furoyloxy)-1,3-imidazolidin-2-one.

EXAMPLE 21

Preparation of 1-(5-Bromothiazol-2-yl)-3-methyl-5-(4-methyl-2-furoyloxy)-1,3-imidazolidin-2-one 1-(5-Bromothiazol-2-yl)-3-methyl-5-hydroxy-1,3-imidazolidin-2-one (0.2 mole), triethylamine (0.25 mole) and benzene (300 ml) are charged into a glass reaction vessel equipped with a mechanical stirrer, thermometer and reflux condenser. 4-Methyl-2-furoyl chloride (0.21 mole) is added dropwise with stirring. After the addition is completed, the reaction mixture is heated with continued stirring for a period of about 45 minutes. After this time the reaction mixture is filtered, and the filtrate is stripped of solvent under reduced pressure to yield a solid residue. This residue is recrystallized to yield the desired product 1-(5-bromothiazol-2-yl)-3-methyl-5-(4-methyl-2-furoyloxy)-1,3-imidazolidin-2-one.

EXAMPLE 22

Preparation of 1-(5-Bromothiazol-2-yl)-3-methyl-5-(3-chloro-2-furoyloxy)-1,3-imidazolidin-2-one 1-(5-Bromothiazol-2-yl)-3-methyl-5-hydroxy-1,3-imidazolidin-2-one (0.2 mole), triethylamine (0.25 mole) and benzene (300 ml) are charged into a glass reaction vessel equipped with a mechanical stirrer, thermometer and reflux condenser. 3-Chloro-2-furoyl chloride (0.21 mole) is added dropwise with stirring. After the addition is completed, the reaction mixture is heated with continued stirring for a period of about 45 minutes. After this time the reaction mixture is filtered, and the filtrate is stripped of solvent under reduced pressure to yield a solid residue. This residue is recrystallized to yield the desired product 1-(5-bromothiazol-2-yl)-3-methyl-5-(3-chloro-2-furoyloxy)-1,3-imidazolidin-2-one.

EXAMPLE 23

Preparation of 1-(5-Bromothiazol-2-yl)-3-methyl-5-(5-methylthien-2-ylcarbonyloxy)-1,3-imidazolidin-2-one 1-(5-Bromothiazol-2-yl)-3-methyl-5-hydroxy-1,3-imidazolidin-2-one (0.2 mole), triethylamine (0.25 mole) and benzene (300 ml) are charged into a glass reaction vessel equipped with a mechanical stirrer, thermometer and reflux condenser. 5-Methylthiophene-2-carboxylic acid chloride (0.21 mole) is added dropwise with stirring. After the addition is completed, the reaction mixture is heated with continued stirring for a period of about 45 minutes. After this time the reaction mixture is filtered, and the filtrate is stripped of solvent under reduced pressure to yield a solid residue. This residue is recrystallized to yield the desired product 1-(5-bromothiazol-2-yl)-3-methyl-5-(5-methylthien-2-ylcarbonyloxy)-1,3-imidazolidin-2-one.

EXAMPLE 24

Preparation of 1-(5-Bromothiazol-2-yl)-3-methyl-5-[4-(3,4-dimethylthien-2-yl)butanoyloxy]-1,3-imidazolidin-2-one 1-(5-Bromothiazol-2-yl)-3-methyl-5-hydroxy-1,3-imidazolidin-2-one (0.2 mole), triethylamine (0.25 mole) and benzene (300 ml) are charged into a glass reaction vessel equipped with a mechanical stirrer, thermometer and reflux condenser. 4-(3,4-Dimethylthien-2-yl)butanoyl chloride (0.21 mole) is added dropwise with stirring. After the addition is completed, the reaction mixture is heated with continued stirring for a period of about 45 minutes. After this time the reaction mixture is filtered, and the filtrate is stripped of solvent under reduced pressure to yield a solid residue. This residue is recrystallized to yield the desired product 1-(5-bromothiazol-2-yl)-3-methyl-5-[4-(3,4-dimethylthien-2-yl)butanoyloxy]-1,3-imidazolidin-2-one.

Additional compounds within the scope of the present invention which can be prepared according to the procedures detailed in the foregoing examples include 1-(5-bromothiazol-2-yl)-3-methyl-5-(4-ethyl-2-furoyloxy)-1,3-imidazolidin-2-one, 1-(5-ethylsulfonylthiazol-2-yl)-3-ethyl-5-(3-iodo-2-furoyloxy)-1,3-imidazolidin-2-one, 1-(5-propylsulfonylthiazol-2-yl)-3-propyl-5-(3-fluoro-2-furoyloxy)-1,3-imidazolidin-2-one, 1-(5-butylsulfonylthiazol-2-yl)-3-butyl-5-(4-bromo-2-furoyloxy)-1,3-imidazolidin-2-one, 1-(5-pentylsulfonylthiazol-2-yl)-3-hexyl-5-(5-propyl-3-furoyloxy)-1,3-imidazolidin-2-one, 1-(5-hexysulfonylthiazol-2-yl)-3-$\gamma$-chloropropyl-5-(4-butyl-3-furoyloxy)-1,3-imidazolidin-2-one, 1-(5-bromothiazol-2-yl)-3-$\delta$-bromobutyl-5-(4-hexyl-3-furoyloxy)-1,3-imidazolidin-2-one, 1-(5-bromothiazol-2-yl)-3-$\omega$-chlorohexyl-5-(3-iodothien-2-ylcarbonyloxy)-1,3-imidazolidin-2-one, 1-(5-bromothiazol-2-yl)-3-but-3-enyl-5-(3-fluorothien-2-ylcarbonyloxy)-1,3-imidazolidin-2-one, 1-(5-bromothiazol-2-yl)-3-pent-4-enyl-5-(4-bromothien-2-ylcarbonyloxy)-1,3-imidazolidin-2-one, 1-(5-bromothiazol-2-yl)-3-hex-4-enyl-5-(5-propylthien-3-ylcarbonyloxy)-1,3-imidazolidin-2-one, 1-(5-bromothiazol-2-yl)-3-but-3-ynyl-5-(4-butylthien-3-ylcarbonyloxy)-1,3-imidazolidin-2-one, 1-(5-bromothiazol-2-yl)-3-pent-4-ynyl-5-(4-hexylthien-3-ylcarbonyloxy)-1,3-imidazolidin-2-one, 1-(5-bromothiazol-2-yl)-3-hex-4-ynyl-5-(3,4-dichloro-2-furoyl-oxy)-1,3-imidazolidin-2-one, 1-(5-bromothiazol-2-yl)-3-methyl-5-(3,4-dibromo-2-furoyloxy)-1,3-imidazolidin-2-one, 1-(5-bromothiazol-2-yl)-3-methyl-5-(3-methyl-4-chloro-2-furoyloxy)-1,3-imidazolidin-2-one, 1-(5-bromothiazol-2-yl)-3-methyl-5-(3-fur-2-ylpropanoyloxy)-1,3-imidazolidin-2-one and the like.

For practical use as herbicides the compounds of this invention are generally incorporated into herbicidal compositions which comprise an inert carrier and a herbicidally toxic amount of such a compound. Such herbicidal compositions, which can also be called formulations, enable the active compound to be applied conveniently to the site of the weed infestation in any desired quantity. These compositions can be solids such as dusts, granules, or wettable powders; or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under super-atmospheric pressure as aerosols. However, preferred liquid herbicidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water in oil) can be prepared for direct application to weed infestations.

A typical herbicidal composition according to this invention is illustrated by the following example, in which the quantities are in parts by weight.

EXAMPLE 25

| Preparation of a Dust | |
|---|---|
| Product of Example 4 | 10 |
| Powdered Talc | 90 |

The above ingredients are mixed in a mechanical grinder-blender and are ground until a homogeneous, free-flowing dust of the desired particle size is obtained. This dust is suitable for direct application to the site of the weed infestation.

The compounds of this invention can be applied as herbicides in any manner recognized by the art. One method for the control of weeds comprises contacting the locus of said weeds with a herbicidal composition comprising an inert carrier and as an essential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about 0.05 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers, spreaders, deactivators, adhesives, stickers, fertilizers, activators, synergists, and the like.

The compounds of the present invention are also useful when combined with other herbicides and/or defoliants, dessicants, growth inhibitors, and the like in the herbicidal compositions heretofore described. There other materials can comprise from about 5% to about 95% of the active ingredients in the herbicidal compositions. Use of combinations of these other herbicides and/or defoliants, dessicants, etc. with the compounds of the present invention provide herbicidal compositions which are more effective in controlling weeds and often provide results unattainable with separate compositions of the individual herbicides. The other herbicides, defoliants, dessicants and plant growth inhibitors, with which the compounds of this invention can be used in the herbicidal compositions to control weeds, can include chlorophenoxy herbicides such as 2,4-D, 2,4,5-T, MCPA, MCPB, 4(2,4-DB), 2,4-DEB, 4-CPB, 4-CPA, 4-CPP, 2,4,5-TB, 2,4,5-TES, 3,4-DA, silvex and the like; carbamate herbicides such as IPC, CIPC, swep, barban, BCPC, CEPC, CPPC, and the like; thiocarbamate and dithiocarbamate herbicides such as CDEC, metham sodium, EPTC, diallate, PEBC, perbulate, vernolate and the like; substituted urea herbicides such as norea, siduron, dichloral urea, chloroxuron, cycluron, fenuron, monuron, monuron TCA, diuron, linuron, monolinuron, neburon, buturon, trimeturon and the like; symmetrical triazine herbicides such as simazine, chlorazine, atraone, desmetryne, norazine, ipazine, prometryn, atrazine, trietazine, simetone, prometone, propazine, ametryne and the like; chloroacetamide herbicides such as alpha-chloro-N,N-dimethylacetamide, CDEA, CDAA, alpha-chloro-N-isopropylacetamide, 2-chloro-N-isopropylacetanilide, 4-(chloroacetyl)morpholine, 1-(chloroacetyl)-piperidine and the like; chlorinated aliphatic acid herbicides such as TCA, dalapon, 2,3-dichloropropionic acid, 2,2,3-TPA and the like; chlorinated benzoic acid and phenylacetic acid herbicides such as 2,3,6-TBA, 2,3,5,6-TBA, dicamba, tricamba, amiben, fenac, PBA, 2-methoxy-3,6-dichlorophenyl-acetic acid, 3-methoxy-2,6-dichlorophenylacetic acid, 2-methoxy-3,5,6-trichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlobenil, DPA, diphenamid, dipropalin, trifluralin, solan, dicryl, merphos, DMPA, DSMA, MSMA, potassium azide, acrolein, benefin, bensulide, AMS, bromacil, 2-(3,4-dichlorophenyl)-4-methyl-1,2,4-oxadiazolidine-3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-l, H-732, M-2901, planavin, sodium tetraborate, calcium cyanamid, DEF, ethyl xanthogen disulfide, sindone, sindone B, propanil and the like. Such herbicides can also be used in the methods and compositions of this invention in the form of their salts, esters, amides, and other derivatives whenever applicable to the particular parent compounds.

Weeds are undesirable plants growing where they are not wanted, having no economic value, and interfering with the production of cultivated crops, with the growing of ornamental plants, or with the welfare of livestock. Many types of weeds are known, including annuals such as pigweed, lambsquarters, foxtail, crabgrass, wild mustard, field pennycress, ryegrass, goose grass, chickweed, wild oats, velvetleaf, purslane, barnyardgrass, smartweed, knotweed, cocklebur, wild buckwheat, kochia, medic, corn cockle, ragweed, sowthistle, coffeeweed, croton, cuphea, dodder, fumitory, groundsel, hemp nettle, knawel, spurge, spurry, emex, jungle rice, pondweed, dog fennel, carpetweed, morningglory, bedstraw, ducksalad, naiad, cheatgrass, fall panicum, jimsonweed, witchgrass, switchgrass, watergrass, teaweed, wild turnip and sprangletop; biennials such as wild carrot, matricaria, wild barley, campion, chamomile, burdock, mullein, roundleaved mallow, bull thistle, hounds-tongue, moth mullein and purple star thislte; or perennials such as white cockle, perennial ryegrass, quackgrass, Johnsongrass, Canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cattail, winter-cress, horsenettle, nutsedge, milkweed and sicklepod.

Similarly, such weeds can be classified as broadleaf or grassy weeds. It is economically desirable to control the growth of such weeds without damaging beneficial plants or livestock.

The new compounds of this invention are particularly valuable for weed control because they are toxic to many species and groups of weeds while they are relatively nontoxic to many beneficial plants. The exact amount of compound required will depend on a variety of factors, including the hardiness of the particular weed species, weather, type of soil, method of application, the kind of beneficial plants in the same area and the like. Thus, while the application of up to only about one or two ounces of active compound per acre may be sufficient for good control of a light infestation of weeds growing under adverse conditions, the application of ten pounds or more of an active compound per acre may be required for good control of a dense infestation of hardy perennial weeds growing under favorable conditions.

The herbicidal toxicity of the new compounds of this invention can be demonstrated by the following established testing techniques known to the art, pre- and post-emergence testing.

The herbicidal activity of the compounds of this invention can be demonstrated by experiments carried out for the pre-emergence control of a variety of weeds. In these experiments small plastic greenhouse pots filled with dry soil are seeded with the various weed seeds. Twenty-four hours or less after seeding the pots are sprayed with water until the soil is wet and a test compound formulated as an aqueous emulsion of an acetone solution containing emulsifiers is sprayed at the desired concentrations on the surface of the soil.

After spraying, the soil containers are placed in the greenhouse and provided with supplementary heat as required and daily or more frequent watering. The plants are maintained under these conditions for a period of from 15 to 21 days, at which time the condition of the plants and the degree of injury to the plants is rated on a scale of from 0 to 10, as follows: 0 = no injury, 1,2 = slight injury, 3,4 = moderate injury, 5,6 = moderately severe injury, 7,8,9 = severe injury and 10 = death.

The herbicidal activity of the compounds of this invention can also be demonstrated by experiments carried out for the post-emergence control of a variety of weeds. In these experiments the compounds to be tested are formulated as aqueous emulsions and sprayed at the desired dosage on the foliage of the weeds that have attained a prescribed size. After spraying the plants are placed in a greenhouse and watered daily or more frequently. Water is not applied to the foliage of the treated plants. The severity of the injury is determined 10 to 15 days after treatment and is rated on the scale of from 0 to 10 heretofore described.

We claim:

1. A compound of the formula

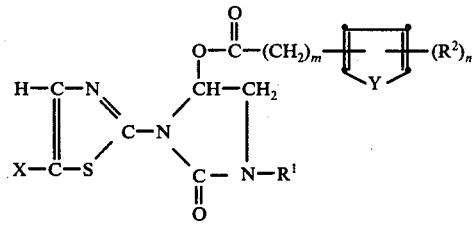

wherein X is selected from the group consisting of chlorine, bromine, fluorine, and lower alkylsulfonyl; $R^1$ is selected from the group consisting of lower alkyl, lower alkenyl, lower haloalkyl and propargyl; m is an integer from 0 to 3; Y is selected from the group consisting of oxygen and sulfur; $R^2$ is selected from the group consisting of lower alkyl, chlorine, bromine, fluorine; and n is an integer from 0 to 2.

2. The compound of claim 1, 1-(5-bromothiazol-2-yl)-3-methyl-5-(2-furoyloxy)-1,3-imidazolidin-2-one.

3. The compound of claim 1, 1-(5-chlorothiazol-2-yl)-3-ethyl-5-(2-thienylcarbonyloxy)-1,3-imidazolidin-2-one.

4. The compound of claim 1, 1-(5-fluorothiazol-2-yl)-3-allyl-5-(fur-2-ylacetyloxy)-1,3-imidazolidin-2-one.

5. The compound of claim 1, 1-(5-iodothiazol-2-yl)-3-propargyl-5-(4-fur-2-ylbutanoyloxy)-1,3-imidazolidin-2-one.

6. The compound of claim 1, 1-(5-methylsulfonylthiazol-2-yl)-3-β-bromoethyl-5-(3-furoyloxy)-1,3-imidazolidin-2-one.

7. The compound of claim 1, 1-(5-bromothiazol-2-yl)-3-methyl-5-(4-methyl-2-furoyloxy)-1,3-imidazolidin-2-one.

8. The compound of claim 1, 1-(5-bromothiazol-2-yl)-3-methyl-5-(3-chloro-2-furoyloxy)-1,3-imidazolidin-2-one.

9. The compound of claim 1, 1-(5-bromothiazol-2-yl)-3-methyl-5-(5-methylthien-2-ylcarbonyloxy)-1,3-imidazolidin-2-one.

* * * * *